United States Patent
Kalder et al.

(10) Patent No.: US 6,183,765 B1
(45) Date of Patent: Feb. 6, 2001

(54) SILICON ELASTOMERS WITH INSECTICIDAL EFFECT

(75) Inventors: Dietmar Kalder, Langenfeld; Alfons Mrozek, Leverkusen, both of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/194,092

(22) PCT Filed: May 15, 1997

(86) PCT No.: PCT/EP97/02490

§ 371 Date: Nov. 20, 1998

§ 102(e) Date: Nov. 20, 1998

(87) PCT Pub. No.: WO97/45011

PCT Pub. Date: Dec. 4, 1997

(30) Foreign Application Priority Data

May 28, 1996 (DE) .............................................. 196 21 304

(51) Int. Cl.[7] .............................. A01N 25/18; A01N 53/00
(52) U.S. Cl. .......................... 424/405; 424/409; 424/486
(58) Field of Search ................... 424/405, 409, 424/484, 486

(56) References Cited

U.S. PATENT DOCUMENTS

| | | | |
|---|---|---|---|
| 3,261,801 | 7/1966 | Wormuth | 260/37 |
| 3,468,838 | 9/1969 | Loraine et al. | 260/37 |
| 3,865,778 | 2/1975 | Christie | 260/37 SB |
| 4,172,904 | * 10/1979 | Young et al. | 427/4 |
| 4,301,056 | 11/1981 | Patzke et al. | 260/37 SB |
| 4,548,999 | 10/1985 | Steinberger et al. | 525/453 |
| 5,219,922 | 6/1993 | Steinberger et al. | 524/785 |
| 5,645,845 | 7/1997 | Neumann et al. | 424/405 |
| 5,705,175 | * 1/1998 | Johnson | 424/409 |
| 5,856,271 | * 1/1999 | Cataldo et al. | 504/116 |

FOREIGN PATENT DOCUMENTS

| | | | |
|---|---|---|---|
| 2911352 | 10/1980 | (DE) | C08L/83/04 |
| 2919338 | 11/1980 | (DE) | A01N/25/00 |
| 4014310A1 | 11/1991 | (DE) | C08L/83/04 |
| 4424786A1 | 1/1996 | (DE) | A01N/53/00 |
| 0010708 | 5/1980 | (EP) | C08L/83/04 |
| 0321279 | 6/1989 | (EP) | A47K/5/12 |
| 0338732 | 10/1989 | (EP) | A01N/25/10 |
| 0356354 | 2/1990 | (EP) | A01N/25/10 |
| 9117215 | 11/1991 | (WO) | C08L/83/10 |

* cited by examiner

Primary Examiner—Robert H. Harrison
(74) Attorney, Agent, or Firm—Norris McLaughlin & Marcus P.A.

(57) ABSTRACT

The invention relates to insecticidal silicone elastomers, processes for their preparation and their use for controlling or repelling insects, in particular in interiors, characterized in that they comprise at least one type of a pyrethroid insecticide which is incorporated in a suitable silicone elastomer.

7 Claims, No Drawings

SILICON ELASTOMERS WITH INSECTICIDAL EFFECT

The invention relates to insecticidal silicone elastomers, processes for their preparation and their use for controlling or repelling insects, in particular in interior spaces. These novel compositions are characterized in that they contain at least one type of insecticide which is incorporated in a suitable silicone elastomer.

The silicone elastomers according to the invention are characterized in that they are capable of releasing the insecticides comprised in them, with or without heating, without changing their form in the process. Thus, optimum effectiveness and duration of action is achieved while the energy input is kept low. This novel insecticidal formulation is to be employed against all flying insects, in particular mosquitos, biting flies, etc., without using a container of any form, optionally by warming the suitable insecticide-comprising silicone elastomer in a suitable heating device.

In the case where for example mosquitos are killed using an electrical heating device, a so-called tablet vaporizer, it is known that suitable materials, such as pulp or cotton cardboard, asbestos or ceramic are impregnated with pyrethroid insecticides to obtain insecticide tablets. The insecticides are volatilized by the action of a heating device generating temperatures of 120–190° C. The gel evaporator is based on a similar principle, the insecticide being incorporated in a gel formulation.

Another method for controlling for example mosquitos is the use of so-called liquid evaporators where an insecticidal liquid formulation is evaporated continuously via a wick system by warming.

A considerable disadvantage of all these prior-art evaporation principles is furthermore the fact that the user may come into contact with the active compound or the active compound formulation, for example by the liquid formulation in liquid vaporizers leaking or by small children chewing and swallowing the paper tablets for tablet vaporizers.

A further disadvantage of the prior-art vaporizer systems mentioned is the non-uniform release of active compound. Additionally, the duration of action of tablet vaporizers is limited to a maximum of 12 hours.

The present invention relates to silicone-based insecticidal elastomers which do not have the above-described disadvantages and are, in addition, easy to use, for example incorporated as a polymer block in known aluminum pans (EP 0 321 279) or as a polymer block directly on the surface of the heater of known vaporization devices, like those used for gel vaporizers (EP 0 321 279). Thus, a continuous release rate is achieved at a low working temperature of 60 to 150° C., preferably 80–120° C.

The silicone elastomers having insecticidal action according to the invention include mixtures comprising at least one silicone elastomer and at least one type of an active pyrethroid compound.

Suitable silicone elastomers which can be prepared by crosslinking of organopolysiloxane materials using a hydroxysilylation reaction of vinyl-containing siloxanes in the presence or absence of platinum catalysts or by using alkoxysilanes in the presence or absence of tin compounds, and the preparation of such suitable silicone elastomers, are disclosed in German Offenlegungsschrift DE-A-40 14 310.

Suitable silicone elastomers based on organosilicone materials which are crosslinkable to elastomers using organic peroxide compounds, and their preparation, represent the prior art, cf. U.S. Pat. Nos. 3,261,801, 3,468,838 and 3,865,778.

Suitable silicone elastomers based on organosilicone materials which are crosslinked using at least one basic inorganic solid are disclosed in German Offenlegungsschrift DE-A-29 11 352.

Suitable silicone elastomers based on organosilicone materials crosslinked by adding polycarbodiimide polysiloxane copolymers are disclosed in European Patent Application EP-A-00 10 708.

The following are preferred as active pyrethroid compounds:

1) natural pyrethrum,
2) 3-allyl-2-methyl-cyclopent-2-en-4-on-1-yl d/l-cis/trans-chrysanthemate (allethrin, Pynamin®),
3) 3-allyl-2-methyl-cyclopent-2-en-4-on-1-yl d-cis/trans-chrysanthemate (Pynamin forte®),
4) d-3-allyl-2-methyl-cyclopent-2-en-4-on-1-yl d-trans-chrysanthemate (Exrin®),
5) 3-allyl-2-methyl-cyclopent-2-en-4-on-1-yl d-trans-chrysanthemate (Bioallethrin®),
6) N-(3,4,5,6-tetrahydrophthalimido)-methyl dl-cis/trans-chrysanthemate, (phthalthrin, Neopynamin®),
7) 5-benzyl-3-furylmethyl d-cis/trans-chrysanthemate (resmethrin, Chrysronforte®),
8) 5-(2-propargyl)-3-furylmethyl chrysanthemate (Furamethrin®),
9) 3-phenoxybenzyl 2,2-dimethyl-3-(2,2-dichlorovinyl)-cyclopropanecarboxylate (permethrin, Exmin®),
10) phenoxybenzyl d-cis/trans-chrysanthemate (phenothrin, Sumithrin®),
11) α-cyanophenoxybenzylisopropyl-4-chlorophenyl acetate (fenvalerate, Sumicidin®),
12) (S)-α-cyano-3-phenoxybenzyl (1R,cis)-3-(2,2-dichlorovinyl)-2,2-dimethylcyclopropanecarboxylate,
13) (R,S)-α-cyano-3-phenoxybenzyl (1R,1S)-cis/trans-3-(2,2-dichlorovinyl)-2,2-dimethylcyclopropanecarboxylate,
14) α-cyano-3-phenoxybenzyl d-cis/trans-chrysanthemate,
15) 1-ethinyl-2-methyl-2-pentenyl cis/trans-chrysanthemate,
16) 1-ethinyl-2-methyl-2-pentenyl 2,2-dimethyl-3-(2-methyl-1-propenyl)-cyclopropane-1-carboxylate,
17) 1-ethinyl-2-methyl-2-pentenyl 2,2,3,3-tetramethylcyclopropanecarboxylate,
18) 1-ethinyl-2-methyl-2-pentenyl 2,2-dimethyl-3-(2,2-dichlorovinyl) cyclopropane-1-carboxylate,
19) (1R)-3-propargyl-2-methyl-cyclopent-2-en-4-on-1-yl cis/trans-chrysanthemate (prallethrin)
20) 2,3,5,6-tetrafluorobenzyl (+)-1R-trans-2,2-dimethyl-3-(2,2-dichlorovinyl)-cyclo-propanecarboxylate (transfluthrin, Bayothrin®) or mixtures of these active compounds.

The active compounds 3-allyl-2-methyl-cyclopent-2-en-4-on-1-yl d-cis/transchryanthemate (Pynamin forte®) and 2,3,5,6-tetrafluorobenzyl (+)-1R-trans-2,2-dimethyl-3-(2,2-dichlorovinyl)-cyclopropane-carboxylate (transfluthrin) are particularly preferred.

Suitable fillers for the compounds according to the invention are for example finely divided pyrogenic or precipitated silicas having a BET surface area of 50 to 500 m$^2$/g. Such fillers may be surface-modified, for example with organosilicon compounds. The modification can also be carried out during incorporation into the polymer by adding for example hexamethyldisilazane or 1,3-divinyl-1,1,3,3-tetramethyldisilazane.

Furthermore, substances such as for example diatomaceous earth, finely divided quartz meals, amorphous silicas or carbon blacks may be incorporated as fillers.

Furthermore, additives such as, for example, organic or inorganic auxiliaries may be incorporated in the mixtures according to the invention, for example as stabilizers, colorants or perfumes.

Suitable organic and inorganic auxiliaries are:

Ammonium salts and ground natural rocks such as kaolins, clays, talc, chalk, quartz, attapulgite, montmorillonte or diatomaceous earth, and ground synthetic minerals, such as finely divided silica, alumina, titania and silicates; as solid carriers for granules there are suitable:

for example crushed and fractionated natural rocks such as calcite, marble, pumice, sepiolite, dolomite, and synthetic granules of inorganic and organic meals, as well as granules of organic material, such as sawdust, coconut shells, maize cobs and tobacco stalks; as emulsifying or foam-forming agents there are suitable:

for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and albumen hydrolysates; as dispersants there are suitable:

for example lignin-sulfite waste liquors and methylcellulose.

Adhesives such as carboxymethylcellulose and natural and synthetic polymers in the form of powders, granules or latices, such as gum arabic, polyvinyl alcohol, polyvinyl acetate, as well as natural phospholipids, such as cephalins and lecithins, and synthetic phospholipids can be used in the insecticide-comprising silicone elastomers according to the invention. Other additives can be mineral and vegetable oils.

It is possible to use colorants such as inorganic pigments, such as iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Deodorants, such as, for example, lauryl methacrylate, geranyl crotonate, acetophenone myristate, p-methylacetophenone benzaldehyde, benzyl acetate, benzyl propionate, amyl cinnamaldehyde, anisaldehyde, diphenyl oxide, methyl benzoate, ethyl benzoate, methylphenyl acetate, ethylphenyl acetate, neoline, safrole, and the like, may be added to the formulations according to the invention.

Other substances which can furthermore be added to the formulations according to the invention are natural perfumes such as, for example, musk, civet, ambergris, castoreum and similar perfumes; ajowa oil, almond oil, absolute of amberseed, angelica root oil, aniseed oil, basil oil, bay oil, benzoin resinoid, essence of bergamot, birch oil, rosewood oil, absolute of common broom, cajeput oil, cananga oil, capsicum oil, caraway oil, cardamom oil, carrot seed oil, cassia oil, cedar wood oil, celery seed oil, cinnamon bark oil, citronella oil, clary sage oil, clove oil, cognac oil, coriander oil, cubeb oil, camphor oil, dill oil, taragon oil, eucalyptus oil, sweet fennel oil, galbanum resinoid, garlic oil, geranium oil, ginger oil, grapefruit oil, hop oil, absolute of hyacinth, absolute of jasmine, juniper berry oil, labdanum resinoid, bay leaf oil, lavender oil, lemon oil, lemon grass oil, lovage oil, mace oil, mandarin oil, absolute of mimosa, absolute of myrrh, mustard oil, absolute of narcissus, neroli oil, nutmeg oil, absolute of oak moss, olibanun resinoid, onion oil, opoponax resinoid, orange oil, orange flower oil, concrete iris, pepper oil, peppermint oil, Perubalsam, petitgrain oil, pine needle oil, absolute of rose, rose oil, rosemary oil, sandalwood oil, sage oil, spearmint oil, storax oil, thyme oil, balsam of tolu, absolute of tonka bean, absolute of tuberose, turpentine oil, absolute of vanilla pod, vetiver oil, absolute of violet leaves, ylang-ylang oil and similar vegetable oils and the like.

Synthetic perfumes which can be added to the silicone formulations according to the invention are:

pinene, limonene and similar hydrocarbons; 3,3,5-trimethylcyclohexanol, linalool, geraniol, nerol, citronellol, menthol, borneol, borneylmethoxycyclohexanol, benzyl alcohol, anisyl alcohol, cinnamyl alcohol, β-phenylethyl alcohol, cis-3-hexanol, terpineol and similar alcohols; anetholes, musk xylene, isoeugenol, methyleugenol and similar phenols; α-amylcinnamaldehyde, anisaldehyde, n-butyraldehyde, cuminaldehyde, cyclamenaldehyde, decyl aldehyde, isobutyraldehyde, hexaldehyde, heptaldehyde, n-nonyl aldehyde nonadienol, citral, citronellal, hydroxycitronellal, benzaldehyde, methylnonyl acetaldehyde, cinnamaldehyde, dodecanal, α-hexylcinnamaldehyde, undecanal, heliotropin, vanillin, ethylvanillin, and similar aldehydes, methyl amyl ketone, methyl β-naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amyl-butyrolactone, diphenyl oxide, methylphenyl glycidate, nonylacetone, coumarin, cineol, ethylmethylphenyl glycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl caproate, butyl heptylate, octyl caprylate, methyl heptinecarboxylate, methyloctinecarboxylate, isoamyl caprylate, methyl laurate, ethyl myristate, methyl myristate, ethyl benzoate, benzyl benzoate, methylcarbinylphenyl acetate, isobutylphenyl acetate, methyl cinnamate, styracin, methyl salicylate, ethyl anisate, methyl anthranilate, ethyl pyruvate, ethyl α-butylbutyrate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethylphenyl acetate, ethylene brassylate, geranyl acetate, geranyl formate, isoamyl salicylate, isoamyl valerate, isobornyl acetate, linalyl acetate, methyl anthranilate, methyl dihydrojasmonate, nonyl acetate, β-phenylethyl acetate, trichloromethylene-phenylcarbinyl acetate, terpinyl acetate, vetiveryl acetate and similar esters.

These can be used on their own, or it is possible to use at least two thereof as a mixture with each other. In addition to perfume, the formulation according to the invention can, if appropriate, additionally comprise the additives conventionally used in the perfume industry, such as patchouli oil or similar volatilization inhibitors, such as eugenol, or similar viscosity regulators.

In addition to the insecticidal active compounds, the silicone elastomers according to the invention can include industrial bactericides and fungicides, such as, for example, 2,4,4-trichloro-2'-hydroxyphenyl ether, 2,3,5,6-tetrachloro-4-(methylsulfonyl)-pyridine, alkylbenzyldimethylammonium chloride, benzyldimethyl-(2)-2-(p-1,1,3,3-tetramethylbutylphenoxy)ethoxy)ethyl) ammonium chloride, 4-isopropyltropolone N-dimethyl-N-phenyl-N-(fluorodichloromethylthio) sulfonamide, 2-(4'-thiazolyl)-benz-imidazole, N-(fluorodichloromethylthio)phthalimide, 6-acetoxy-2,4-dimethyl-m-dioxin, and the like, and bactericides and fungicides used in agriculture, such as, for example, zinc ethylenebisdithiocarbamate, manganese ethylenebisthiocarbamate, zinc maneb complex, bis-dimethyldithiocarbamoyl zinc ethylene bisdithiocarbamate, bis(dimethylthiocarbamoyl) disulfide, 2,6-dinitro-4-octylphenyl crotonate and the like, or repellents such as, for example, dimethyl phthalate, 2,3,4,5-bis-($\Delta_2$-butylene) tetrahydrofuran, 2,3,4,5-bis-($\Delta_2$-butylene) tetrahydrofurfuryl alcohol, N,N-diethyl-m-toluamide (termed "DEET" hereinbelow), caprylic acid, diethylamide, 2,3,4,5-bis($\Delta_2$-butylene) tetrahydrofurfural, di-n-propyl isocinchomeronate, sec-butyl styryl ketone, nonyl styryl ketone, n-propylacetanilide, 2-ethyl-1,3-hexanediol, di-n-butyl succinate, 2-butoxyethyl-2-furfurylidene acetate, dibutyl phthalate, tetrahydrothiophene, β-naphthol, diallyl sulfide, bis(dimethylthiocarbamoyl) disulfide and the like.

The insecticidal elastomers according to the invention can be stabilized with the aid of antioxidants by admixing a UV absorber as an additive. Suitable UV absorbers are all known UV absorbers.

Preferably employed are phenol derivatives such as, for example, butyl hydroxytoluene (BHT), butylhydroxyanisole (BHA), bisphenol derivatives, aryl-amines such as, for example, phenyl-α-naphthylamine, phenyl-β-naphthylamine, a condensate of phenetidine and acetone or the like, or benzophenones.

The compositions according to the invention generally comprise between 0.1 and 80% by weight, preferably between 0.2 and 40% by weight, very preferably between 0.5 and 20% by weight of active compound.

The invention further provides a process for preparing the insecticidal silicone elastomers according to the invention by mixing a basic mixture comprising OH-terminated polydialkylsiloxanes and fillers with very high shear with further OH-terminated polydiallylsiloxane, the desired amount of active compound and a suitable stabilizer. After the addition of a suitable crosslinking catalyst, the compositions obtained are pressed into tablets and cured at a suitable temperature.

The preparation and the use of the insecticidal elastomers according to the invention is illustrated according to the following examples.

EXAMPLES

Example 1

Preparation of an insecticidal elastomer, active compound content 1.5%:

200 g of a base mixture comprising OH-terminated polydimethylsiloxanes of a mean viscosity of 18 Pa.s and a finely divided pyrogenic silica having a surface area of about 300 m$^2$/g (for example Silopren base mixture P 490, Bayer AG (75% polydimethylsiloxan CAS #70-131-67-8; 25% pyrogenic silicic acid CAS #76-31-86-9)) are mixed in a planetary mixer having a capacity of 1 l with 120 g of an OH-terminated polydimethylsiloxane of a mean viscosity of 2 Pa.s (for example Silopren C 2, Bayer AG CAS #70-131-67-8) in three portions of 40 g each, with very high shear (min. 80 rpm) within 30 minutes. After the addition of the polymer, 4.88 g of transfluthrin and 3.28 g of butylhydroxytoluene (BHT) are admixed within 10 minutes. The entire mixture is finally degassed for 2 minutes under reduced pressure.

For crosslinking, 100 g of the premix are stirred with 4 g of crosslinker, for example Silopren C Vernetzer 5, Bayer AG (consisting of 40.0% by weight of tetraethoxysilane (CAS #78-10-4), 32.5% by weight of ethyl polysilicate (CAS #68-412-37-3) and 27.5% of dibutyltin dilaurate CAS #77-58-7)) until a homogeneous material is obtained. The entire mixture is degassed once again for 2 minutes under reduced pressure.

The molds are pretreated with 1% strength aqueous detergent solution as parting agent and cured at room temperature for 72 h.

Example 2

Preparation of an insecticidal elastomer, active compound content 10%:

200 g of a base mixture comprising OH-terminated polydimethylsiloxanes of a mean viscosity of 18 Pa.s and finely divided pyrogenic silica having a surface area of about 300 m$^2$/g are mixed in a planetary mixer having a capacity of 1 l with 120 g of an OH-terminated polydimethylsiloxane of a mean viscosity of 2 Pa.s in three portions of 40 g each, with very high shear (min. 80 rpm) within 30 minutes. After the addition of the polymer, 35.56 g of transfluthrin and 3.6 g of butylhydroxytoluene (BHT) are admixed within 10 minutes. The entire mixture is finally degassed for 2 minutes under reduced pressure.

For crosslinking, 100 g of the premix are stirred with 4 g of crosslinker, for example Silopren C Vernetzer 5, Bayer AG (consisting of 40.0% by weight of tetraethoxysilane, 32.5% by weight of ethyl polysilicate and 27.5% of dibutyltin dilaurate) until a homogeneous material is obtained. The entire mixture is degassed once again for 2 minutes under reduced pressure.

The molds are pretreated with 1% strength aqueous detergent solution as parting agent and cured at room temperature for 72 h.

Example 3

Determination of the release rates:

The release rates were determined using a silicone elastomer prepared by the method of Example 1 having 1.5% active compound content. The elastomer was cured in molds of the dimensions 25 mm×40 mm×4 mm at room temperature for 72 h. The silicone tablets obtained in this manner were heated to 100–110° C. on a heating apparatus of the company Steinel, type MV-1, over 7 cycles of 8 h each.

| Evaporation rates of a silicone elastomer prepared by the method of Example 1 [mg/h] | | |
|---|---|---|
| Cycle | Vaporization oven A | Vaporization oven B |
| 1 | 6.4 | 7.0 |
| 3 | 2.5 | 2.8 |
| 4 | 1.4 | 1.6 |
| 5 | 1.3 | 1.5 |
| 6 | 1.2 | 1.0 |
| 7 | 1.5 | 1.5 |

The evaporation rates obtained exhibit the expected typical course where greater amounts are evaporated in the initial cycles and the evaporation rate balances level out to about 1–2 mg/h in the later cycles.

Example 4

Biological activity

Insecticidal action of the insecticide-comprising silicone elastomers according to the invention in vaporization systems:

Mosquito species: Aedes aegypti
Room size: 34 m³
Type of room: 1 window open
  Temperature: 23–30° C.
  Relative humidity: 23–34%
  Heating temperature: 100–110° C.
  Amount of formulation: 3.5 g
  Content of active compound: 1.6%

| Operating time/ test after days | Introduction of mosquitos after hours | Knock-down effect after min. or h 50% | Knock-down effect after min. or h 100% | % dead after 9 h | % dead after 24 h |
|---|---|---|---|---|---|
| 1 Day 8 Hours | 0 | 47' | 59' | 100 | 100 |
| | 1 | 10' | 24' | 100 | 100 |
| | 2 | 11' | 19' | 100 | 100 |
| | 3 | 19' | 56' | 100 | 100 |
| | 4 | 10' | 15' | 100 | 100 |
| | 5 | 8' | 45' | 100 | 100 |
| | 6 | 9' | 40' | 100 | 100 |
| | 7 | 8' | 16' | 100 | 100 |
| | 8 | 6' | 12' | 100 | 100 |
| 2 Days 16 Hours | 0 | 46' | 1 h 08' | 100 | 100 |
| | 1 | 21' | 45' | 100 | 100 |
| | 2 | 25' | 49' | 100 | 100 |
| | 3 | 23' | 36' | 100 | 100 |
| | 4 | 23' | 44' | 100 | 100 |
| | 5 | 23' | 42' | 100 | 100 |
| | 6 | 22' | 38' | 100 | 100 |
| | 7 | 17' | 26' | 100 | 100 |
| | 8 | 20' | 35' | 100 | 100 |
| 3 Days 24 Hours | 0 | 50' | 59' | 100 | 100 |
| | 1 | 35' | 58' | 100 | 100 |
| | 2 | 40' | 1 h 26' | 100 | 100 |
| | 3 | 39' | 1 h 16' | 100 | 100 |
| | 4 | 34' | 1 h 07' | 100 | 100 |
| | 5 | 35' | 1 h 07' | 100 | 100 |
| | 6 | 24' | 1 h 02' | 100 | 100 |
| | 7 | 19' | 48' | 100 | 100 |
| | 8 | 16' | 40' | 100 | 100 |
| 4 Days 32 Hours | 0 | 1 h 01' | 1 h 31' | 100 | 100 |
| | 1 | 31' | 1 h 04' | 100 | 100 |
| | 2 | 33' | 1 h 11' | 100 | 100 |
| | 3 | 52' | 2 h 20' | 100 | 100 |
| | 4 | 1 h 45' | 2 h 34' | 100 | 100 |
| | 5 | 44' | 1 h 28' | 100 | 100 |
| | 6 | 1 h 12' | 1 h 43' | 100 | 100 |
| | 7 | 25' | 41' | 100 | 100 |
| | 8 | >1 h | >1 h | 55 | 98 |
| 5 Days 40 Hours | 0 | 1 h 04' | 2 h 40' | 100 | 100 |
| | 1 | 29' | 2 h 23' | 100 | 100 |
| | 2 | 36' | 1 h 47' | 100 | 100 |
| | 3 | 41' | 1 h 10' | 100 | 100 |
| | 4 | 41' | 1 h 24' | 100 | 100 |
| | 5 | 31' | 1 h 01' | 100 | 100 |
| | 6 | 22' | 59' | 100 | 100 |
| | 7 | 19' | 36' | 100 | 100 |
| | 8 | >1 h | >1 h | 33 | 98 |
| 6 Days 48 Hours | 0 | 1 h 10' | 1 h 50' | 100 | 100 |
| | 1 | 37' | 1 h 17' | 100 | 100 |
| | 2 | 57' | 1 h 23' | 100 | 100 |
| | 3 | 47' | 1 h 52' | 100 | 100 |
| | 4 | 38' | 1 h 41' | 100 | 100 |
| | 5 | 57' | 1 h 38' | 100 | 100 |
| | 6 | 50' | 1 h 10' | 100 | 100 |
| | 7 | 50' | 1 h 02' | 100 | 100 |
| | 8 | 20' | >1 h | 83 | 86 |
| 7 Tage 56 Hours | 0 | 1 h 02' | 2 h 08' | 100 | 100 |
| | 1 | 1 h 10' | 1 h 59' | 100 | 100 |
| | 2 | 1 h 20' | 2 h 54' | 100 | 100 |
| | 3 | 1 h 03' | 2 h 03' | 100 | 100 |
| | 4 | 44' | 1 h 20' | 100 | 100 |
| | 5 | 45' | 1 h 47' | 100 | 100 |
| | 6 | 48' | 1 h 26' | 100 | 100 |
| | 7 | 53' | >2 h | 90 | 100 |
| | 8 | 22' | >1 h | 78 | 95 |

What is claimed is:

1. Insecticidal silicone elastomers comprising silicone elastomers and insecticidally active compounds selected from the group consisting of transfluthrin, 3-allyl-2-methyl-cyclopent-2-en4-on-1-yl d/l-cis/trans-chrysanthemate, 3-allyl-2-methyl-cyclopent-2-en-4-on-1-yl d-cis-trans-chysanthemate, d-3-allyl-2-methyl-cyclopent-2-en4-on-1-yl d-trans-chrysanthemate, 3-allyl-2-methyl-cyclopent-2-en4-on-1-yl d-trans-chrysanthemate, and mixtures thereof.

2. Insecticidal silicone elastomers according to claim 1, wherein said elastomers are capable of releasing said insecticidally active compounds, with or without heating, without changing their form in the process.

3. Insecticidal silicone elastomers according to claim 1, wherein said elastomers comprise at least one silicone elastomer prepared by crosslinking of organopolysiloxane materials using a hydrosilylation reaction of vinyl-containing siloxanes in the presence or absence of platinum catalysts or using alkoxysilanes in the presence or absence of tin compounds or using organic peroxide compounds or using at least one basic inorganic solid or by adding polycarbodiimide polysiloxane copolymers.

4. Insecticidal silicone elastomers according to claim 1, comprising 0.1 to 80% by weight of active compound.

5. Insecticidal silicone elastomers according to claim 1, comprising finely divided pyrogenic or precipitated silicas having a BET surface area of 50 to 500 m²/g, diatomaceous earth, finely divided quartz meals, amorphous silicas or carbon blacks and stabilizers, colorants or perfumes as fillers.

6. Process for preparing the insecticidal silicone elastomers according to claim 1, wherein a base mixture comprising OH-terminated polydialkylsiloxanes and fillers is mixed with very high shear with further OH-terminated polydialkylsiloxane, the desired amount of active compound and a suitable stabilizer, and the compositions obtained are, after the addition of a suitable crosslinking catalyst, pressed into tablets and cured at a suitable temperature.

7. Method for controlling or repelling flying insects comprising placing an effective amount of the insecticidal silicone elastomers according to claim 1 in the habitat of said insects.

* * * * *

UNITED STATES PATENT AND TRADEMARK OFFICE
CERTIFICATE OF CORRECTION

PATENT NO.    : 6,183,765 B1
DATED         : February 6, 2001
INVENTOR(S)   : Kalder et al.

It is certified that error appears in the above-identified patent and that said Letters Patent is hereby corrected as shown below:

<u>Column 8,</u>
Line 21, delete "chysanthemate" and substitute -- chrysanthemate --

Signed and Sealed this

Twelfth Day of March, 2002

Attest:

Attesting Officer

JAMES E. ROGAN
*Director of the United States Patent and Trademark Office*